United States Patent
Cavanaugh et al.

[19]

[11] Patent Number: 6,086,319

[45] Date of Patent: Jul. 11, 2000

[54] MULTIPLE WELL PLATE STACK EXPANDER

[75] Inventors: Kevin C. Cavanaugh, Sommersworth, N.H.; Adam P. Doiron, Sanford, Me.; Lee A. Ketchum, Biddeford, Me.; Michael J. Leporati, Wells, Me.; James H. Santerre, Kennebunk, Me.; Normand J. Voisine, Biddeford, Me.

[73] Assignee: Corning Incorporated, Corning, N.Y.

[21] Appl. No.: 09/197,292

[22] Filed: Nov. 20, 1998

Related U.S. Application Data

[60] Provisional application No. 60/066,318, Nov. 21, 1997.

[51] Int. Cl.[7] .................................................. B65G 65/04

[52] U.S. Cl. .................... 414/788; 211/1.57; 414/331.16; 414/417; 414/800

[58] Field of Search ............................... 414/331.04, 416, 414/417, 404, 331.16, 788, 795.4, 795.9; 221/87; 211/1.57, 187

[56] References Cited

U.S. PATENT DOCUMENTS

| | | | |
|---|---|---|---|
| 2,779,487 | 1/1957 | Harris | 414/795.4 |
| 3,844,428 | 10/1974 | Olsen | 414/417 |
| 3,940,174 | 2/1976 | Mayes | 211/1.57 |
| 5,423,503 | 6/1995 | Tanaka et al. | 211/1.57 |
| 5,735,662 | 4/1998 | Nichols et al. | 414/331.16 |
| 5,908,776 | 6/1999 | Burbaum et al. | 435/288.3 |

*Primary Examiner*—Gregory A. Morse
*Attorney, Agent, or Firm*—Thomas R. Beall

[57] ABSTRACT

A device and method for expanding the distance between individual multiwell plates of a stack of multiwell plates so that all the plates can be loaded at once into a magazine commonly used in automated analysis systems. Significant to the device are a series of inter-connected rails, each rail capable of supporting one plate. As the distance between the rails is increased, the stack of plates is expanded and will align with slots from a magazine loader. By using the device, a stack can be expanded in preparation for loading, or conversely, plates coming from a magazine can be restacked for storage.

7 Claims, 9 Drawing Sheets

6,086,319

1

MULTIPLE WELL PLATE STACK EXPANDER

This application claims the benefit of U.S. Provisional Application No. 60/066,318, filed Nov. 21, 1997.

FIELD OF THE INVENTION

The invention relates to a laboratory accessory for use in chemical and biological testing and experimentation and, more specifically, to a device that will aid in the feeding of multiple multiwell plates to a loading station as part of an automated analysis system.

BACKGROUND OF THE INVENTION

For many years, multiwell laboratory plates have been manufactured in configurations ranging from 1 to 96 wells, and beyond. The wells of multiwell plates are typically used as reaction vessels for performing various tests, growing tissue cultures, screening drugs, or performing analytical and diagnostic functions. Industry standard multiwell plates are laid out with 96 wells in an 8×12 matrix (mutually perpendicular 8 and 12 well rows). Most multiwell plates also have stepped sidewalls to enable plates to be securely stacked one on another. In addition, the height, length and width of the 96 well plates are standardized. The standardization has resulted in the development of a large array of auxiliary equipment specifically developed for 96 well formats. The equipment includes devices that load and unload precise volumes of liquid in multiples of 8,12, or 96 wells at a time. In addition, equipment is available to transmit light through individual wells and to read colorimetric changes or chemiluminscence in individual wells. Some of the standardized equipment is designed to analyze and manipulate the data recorded.

Automation of analyses in the drug industry has fueled new methods of drug discovery: high throughput screening and combinatorial chemistry. By using these techniques, pools of thousands of compounds having slight chemical variations are screened en masse. Only a small fraction of drug candidates show promise, but by testing thousands or even millions of compounds, the likelihood of stumbling on a compound with promising biological activity is increased.

In order to test these thousands of compounds, drug manufacturers have relied on the industry standard multiwell plate, usually having a format of 96 wells. In order to begin the automated drug screening process, a storage magazine having a plurality of slots (typically 20 or more), each sized to receive a single multiwell plate, is loaded by hand. The plates are thereafter taken by robotic means to various stations where sample manipulations are performed.

The slots in the magazine are spaced such that individual plates may be taken from the slots by means of robotic handling equipment. Currently, the slots in the storage magazine are loaded by manually taking one plate at a time from the manufacturer's shipping carton and loading into the individual slots. Considering the speed at which plates are tested, this process is continuous and time consuming.

SUMMARY OF THE INVENTION

The present invention provides a device that allows a user to load an entire storage magazine with multiwell plates in one step, thereby eliminating the need to load plates one at a time.

The device separates individual plates in a stack of plates such that the spacing between them is substantially equal to

2 the spacing between slots in a storage magazine from an automated analyses system. Once the plates are properly spaced, they can all be transferred simultaneously from the device to a storage magazine in one loading motion. Alternatively, the plates may be shifted from the storage magazine to the device and compacted into stacked form.

The stack separating device comprises a nest enclosed by a housing defining an open front and back, that accepts a stack of multiwell plates, a plurality of expander rails located along the inner walls of the housing and defining slots capable of fitting between successive stepped portions of stacked plates. The expander rails are all inter-connected and attached to a handle, whereby when the handle is pulled upwards, the distance between the expander rails is increased and thereby the distance between the plates is increased.

DETAILED DESCRIPTION OF THE INVENTION

Figure 1:
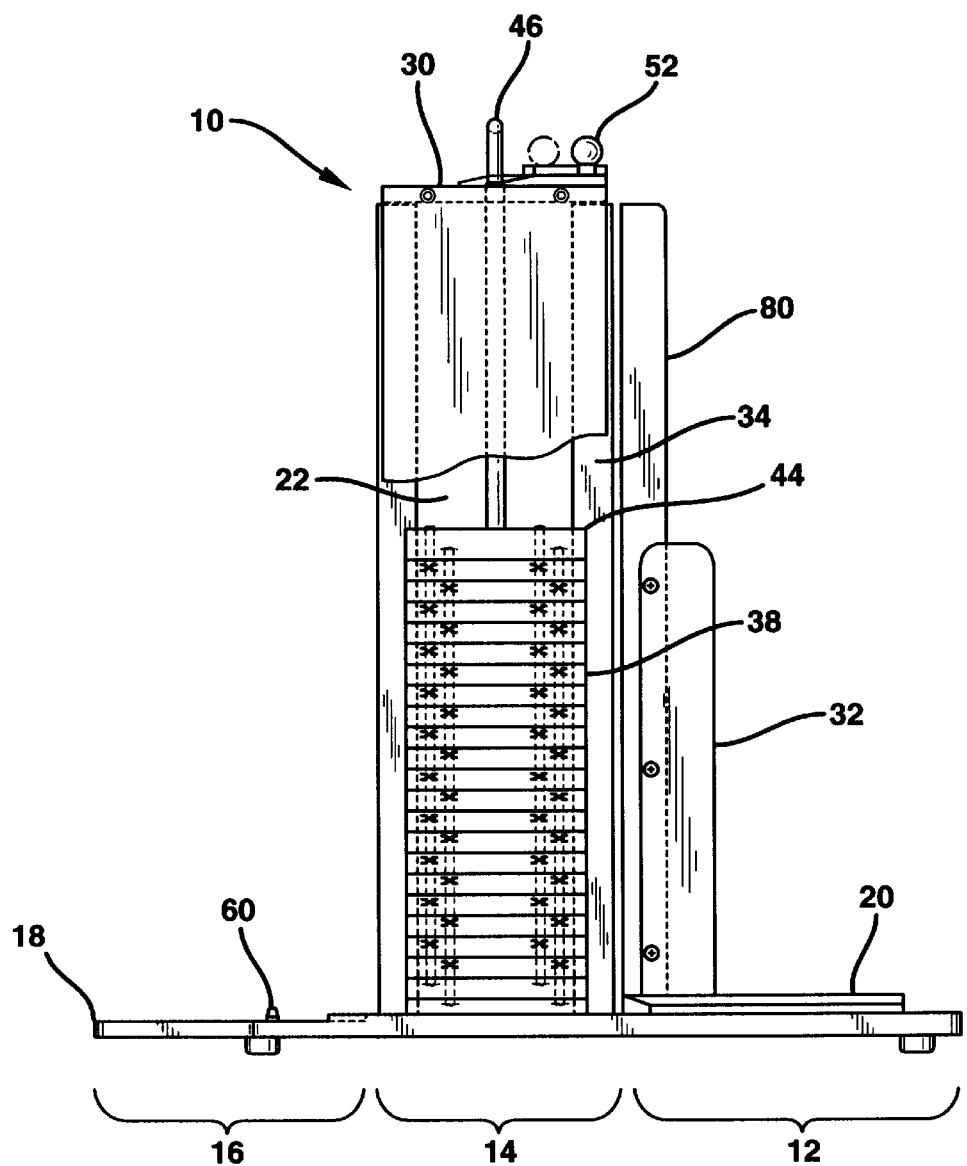
FIG. 1 is a side view of the plate separator of the present invention.

FIGS. 1–4 show various views of the plate separator 10 of the present invention. The apparatus can be divided into three regions: stack loading nest 12, the expander unit 14, and the magazine nest 16. A base 18 extends across the three regions. The stack loading nest 12 has two opposing stack locators 20 mounted on and raised above the surface of the base 18. These raised grooves center a stack of multiwell plates for entry into the expander unit.

The expander unit comprises a housing 22 having opposing walls 24 that define an open front 26 and back 28, and a top 30. The walls 24 of the expander unit 14 are roughly in line with the stack locators 20 and are preferably approximately 20 inches in height, but may vary based on the size of the magazine to be loaded. Stainless steel infeed guides 32 are attached to gate support angles 80 and extend to a height commensurate with a stack of 22 multiwell plates, approximately 10.5 inches. The infeed guides 32 are angled inward, towards the housing 22, such that a stack of plates will be properly aligned upon entering the housing. To the ends of each wall of the housing are attached end caps 34 which are cornered pieces that run the length of the wall 24. One arm of each end cap 34 is attached in a direction perpendicular to the wall. The other arm of each end cap extends into the housing 22 interior creating a vertical slide mount 36.

Fitted horizontally along the interior of the walls 24 and orthogonal to the wall, are 22 pairs of expander rails 38. An example of an expander rail 38 is shown in plan view in FIG. 2A, side view in FIG. 2B, and end view in FIG. 2C. The expander rails each have grooves 40 on opposing ends that fitably engage the vertical slides 36. Each rail 38 has a shelf 39. When engaged by the opposing slide mounts 36, the shelf 39 extends approximately 0.13 inches into the housing interior 22 (approximately the width of the step found on the sidewalls of most stackable multiwell plates). The shelf 39 is preferably beveled on each end to help receive the grooves formed between the step portion of one plate and the bottom of a plate stacked above it in a stack of multiwell plates.

Figure 4:
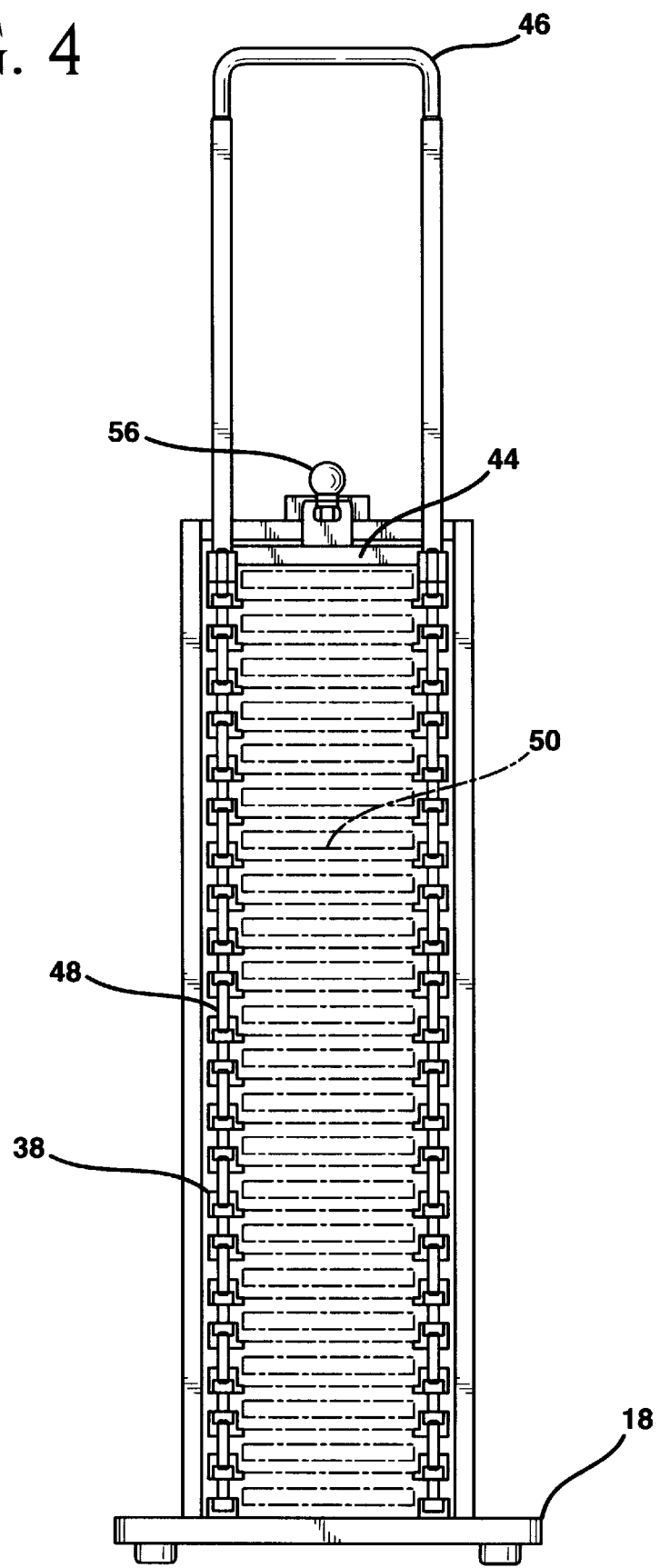
FIG. 4 is a front view of the plate separator of the present invention in the expanded position and showing the stack of FIG. 3, now expanded.
Figure 4A:
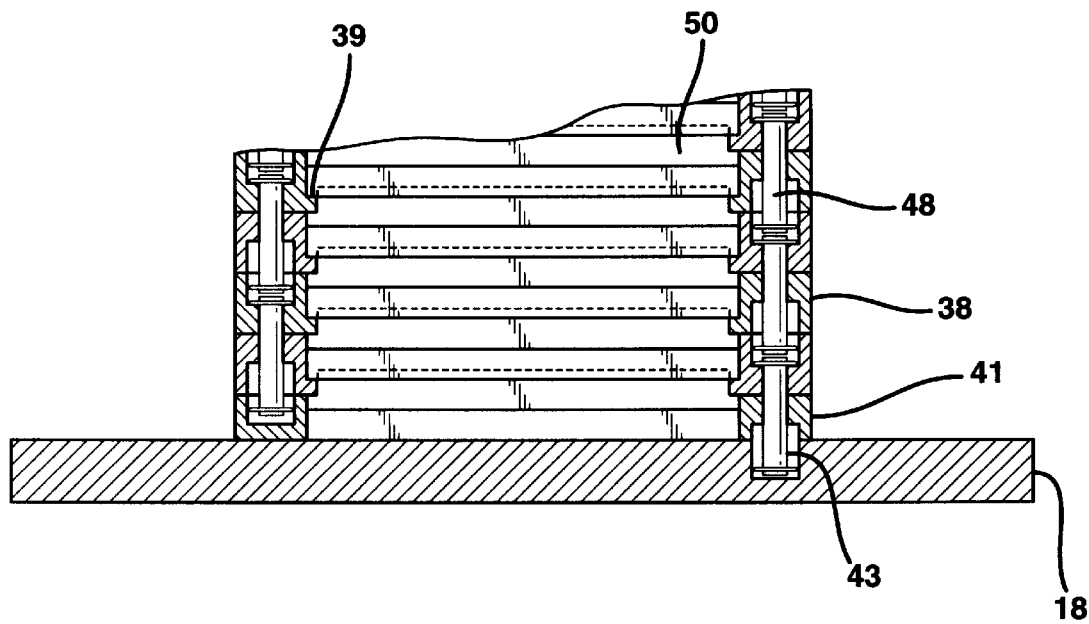
FIG. 4A is a partial cross sectional view the plate separator of the present invention in the collapsed position, and specifically, of the expander rails holding multiwell plates.
Figure 4B:
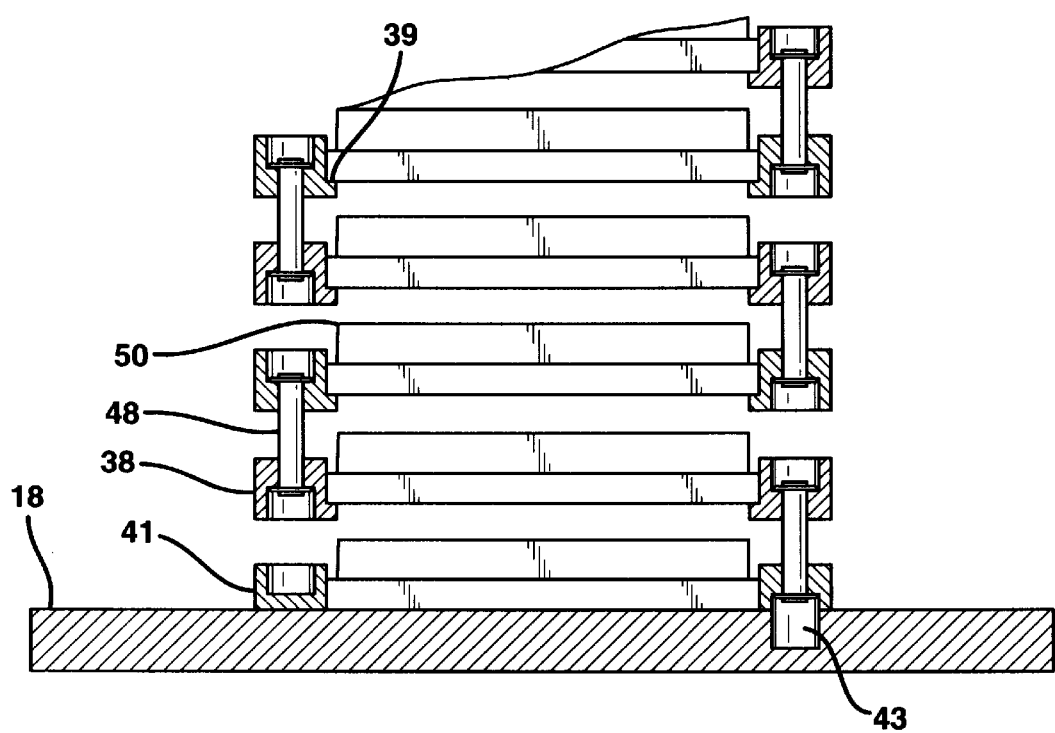
FIG. 4B is a partial cross sectional view the plate separator of the present invention in the expanded position, and specifically, of the expander rails holding multiwell plates.

The expander rails 38 also preferably have a series of holes 42 drilled therethrough for fitting connector pins. Connector pins 48 are situated through holes 42 in each rail 38. On each side of the rail is one pair of holes. One connector pin from each side connects to a corresponding rail located directly above the rail. Likewise, one connector pin from each pair connects to a corresponding rail located directly below the rail. This way, each rail is connected to immediately successive rails by two connector pins. The connector pins are equipped with E-rings on both ends. The E-rings serve to contain the pin ends within the rails and thereby serve to limit the distance the pins can slide within the holes. The holes have a portion having an inner diameter roughly commensurate with the diameter of the E-ring on the connector pin, and a portion roughly commensurate with the diameter of the pin itself. For the expander rail holes that contain the pins that connect to the rail immediately above, the diameter of the hole on the top half of the rail is less than the diameter of the E-ring and roughly commensurate with the diameter of the pin itself (as shown in FIGS. 4A and 4B). This way, when a rail immediately above is lifted, the E-ring slides through the hole to the point in which the hole diameter decreases. The E-ring contacts the hole at this point and the pin therefore cannot be pulled out of the hole. Likewise, for expander rail holes that contain pins that connect to the rail immediately below, the diameter of the hole on the bottom half of the rail is less than the diameter of the E-ring. Further, as shown in FIGS. 4A and 4B, the base plate 18 contains depressions 43 that contain the pins 48 while the expander is in the collapsed position. The pins that fill these depressions connect the bottom most expander rail with an anchor rail attached to the plate.

A top plate 44 having grooves on opposing sides is connected to the uppermost stacked rail. A handle 46 connects to the top plate 44, which when pulled upward, extends the spacing between rails to the width allowed by the connector pins. The distance between the E-rings on the connector pins determines spacing between rails, when the handle is drawn. Therefore, the connector pins 48 should be sized to the plate magazine that is being loaded. For example, when loading a "ZYMARK" magazine, the distance between E-rings on the connector pins should be approximately 0.82 inches in length.

Figure 3:
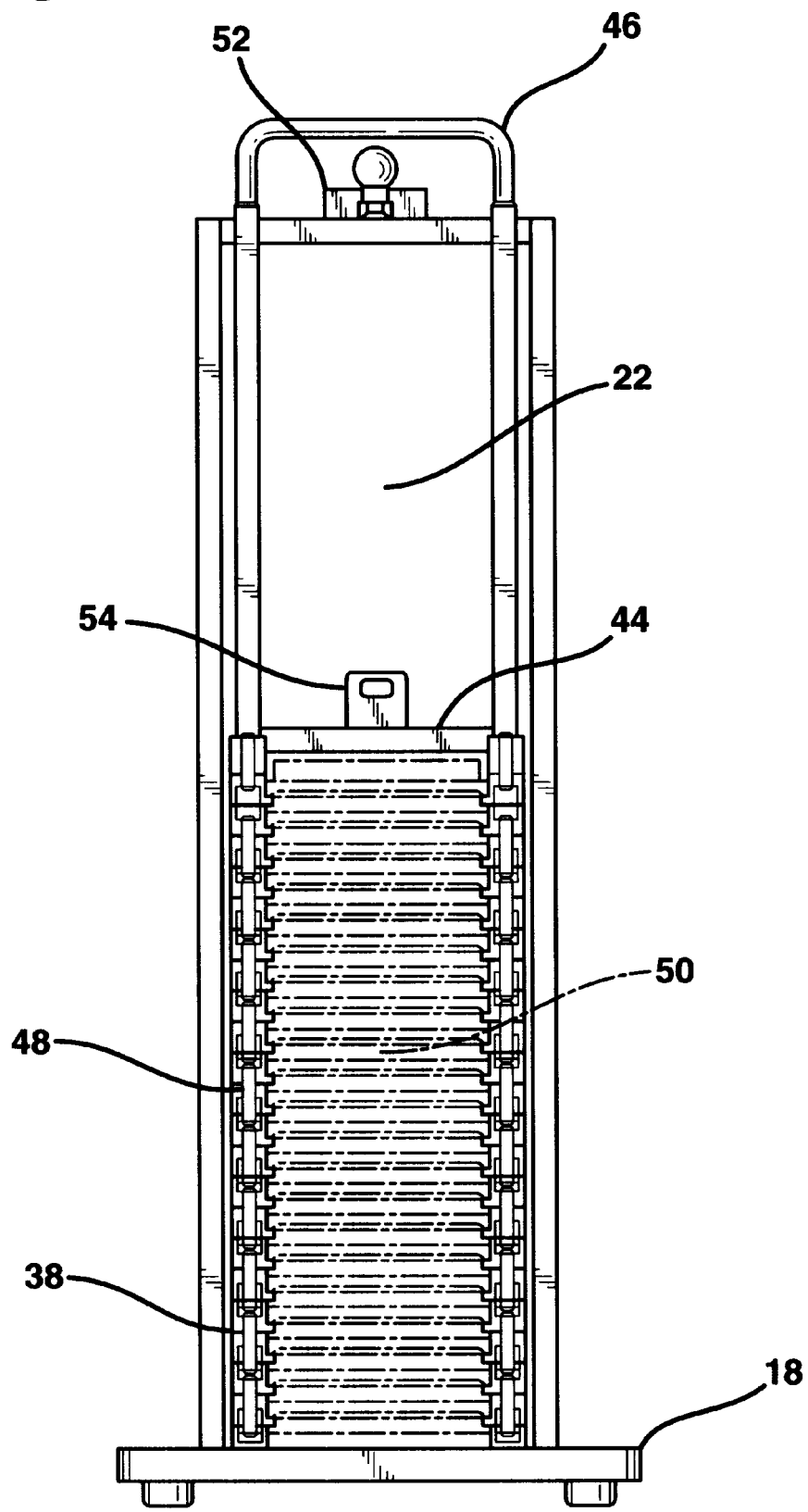
FIG. 3 is a front elevation view of the plate separator of the present invention in the collapsed position and having a stack of well plates loaded within the housing.

FIG. 3 shows the expander unit in the depressed position where the expander rails 38 are stacked upon one another. A stack of plates 50 is located within the housing 22. Each plate bottom rests upon an expander rail step. FIG. 4 shows the expander unit 14 in the extended position where connector pins 48 are holding the expander rails 38 together. The multiwell plates 50 are spaced a distance commensurate with spacing of slots on a magazine loader.

As can be seen in FIG. 4A, a cross section of the expander unit in the collapsed position, the expander rails 38 are stacked upon one another defining slots capable of fitting between stacked multiwell plates 50. An anchor rail 41 is permanently affixed to the base plate 18. FIG. 4A shows multiwell plates SO, stacked one upon another, contacting shelves 39 of the expander rails 38. Rails are connected by connector pins 48. Depressions 43 in the base plate 18 contain the connector pins 48 (two on each side) that connect the anchor rail 41 with the bottommost expander rail 38, while the expander unit is in the collapsed position.

FIG. 4B is a partial cross section of the expander unit in the expanded position. Multiwell plates 50 contact shelves 39 on the expander rails 38. The rails are separated by the length of connector pins 48. The multiwell plates 50 from the stack are now separated apart a distance approximately identical to the distance separating each expander rail 38. Anchor rails 41 do not move upward as they are permanently affixed to the base plate 18.

Figure 7:
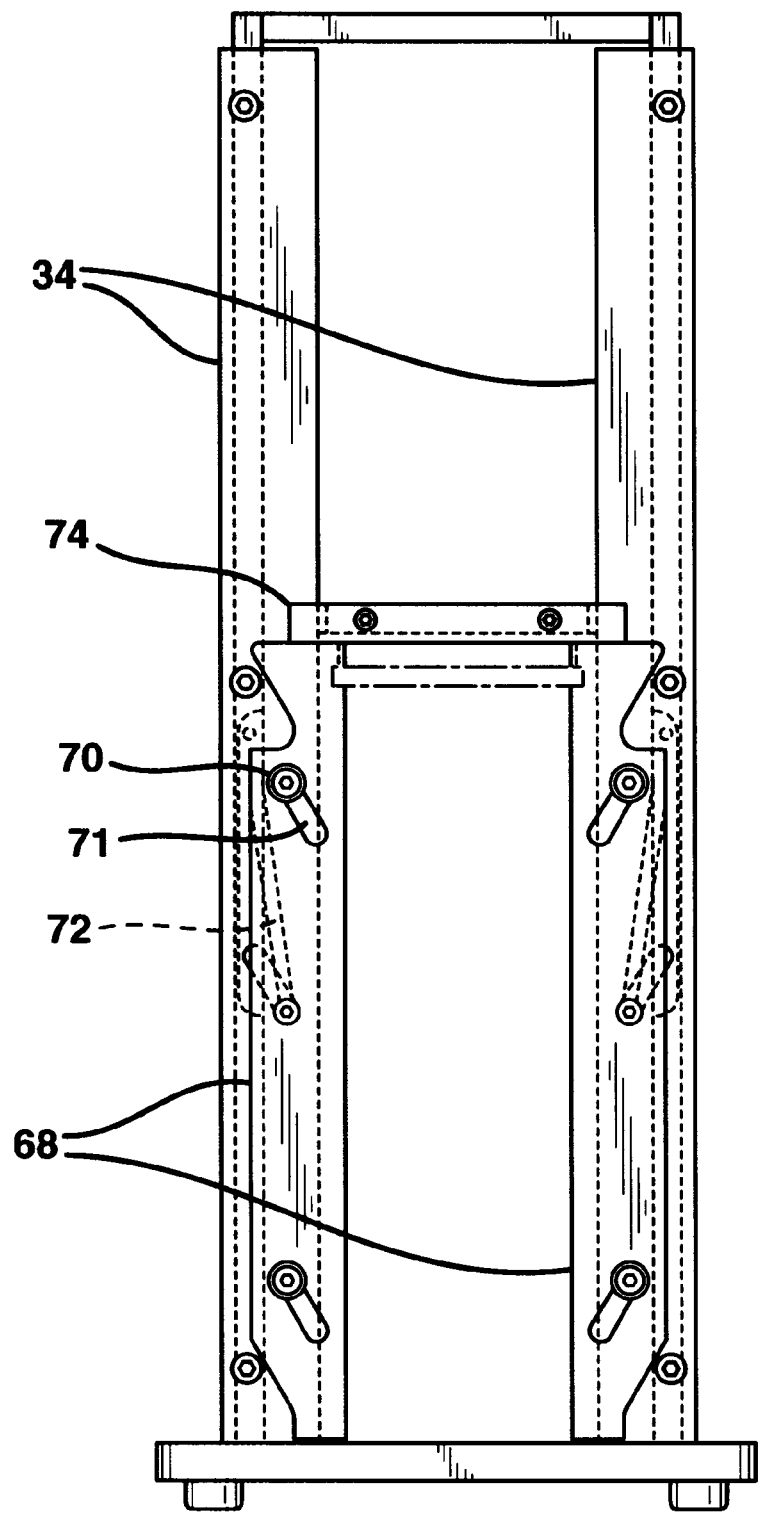
FIG. 7 is a front view of the load limit gates of the present invention.

The device will preferably have a load limit gate and unload limit gate that will prevent plates from being pushed through the expander housing. FIG. 7 is an elevation view of the expander housing looking into the open back area 28. Preferably, a pair of load limit gates 68 are mounted on shoulder screws 70 which attach to the backmost angular end caps 34. The gates fit just loosely enough to freely move up and down along the shoulder screws, limited in travel by the length of each gate slot 71. The two mount slots 71 per gate are at a 30 degree angle thereby allowing each gate to move up and out to increase the housing opening. A tension spring 72 is located behind end cap 34, of both gates, with one end attached to the gate and the other end to the edge of wall 24. The springs load each gate upward. A gate release bar 74 is attached to the moving top plate 44 which, when in the down position, holds each gate down in the closed position (as in FIG. 7). When a stack of plates is pushed into the housing unit from the stack loading nest, the load limit gates create a backstop, beyond which the stack can not be moved. When handle 46 is pulled up for stack expansion, the rise of bar 74 allows the gates 68 to open so that the expanded stack of multiwell plates may be transferred freely between the expander unit housing 22 and the magazine nest 16.

Figure 2:
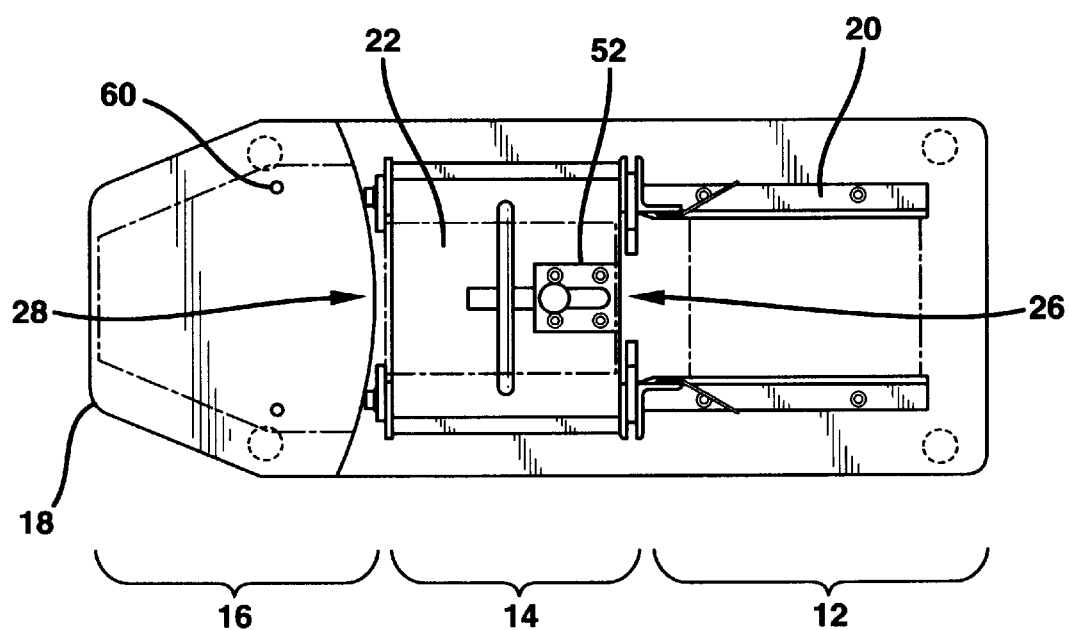
FIG. 2 is a plan view of the plate separator of the present invention along with a section view through the middle of the expander unit of the present invention.
Figure 2A:
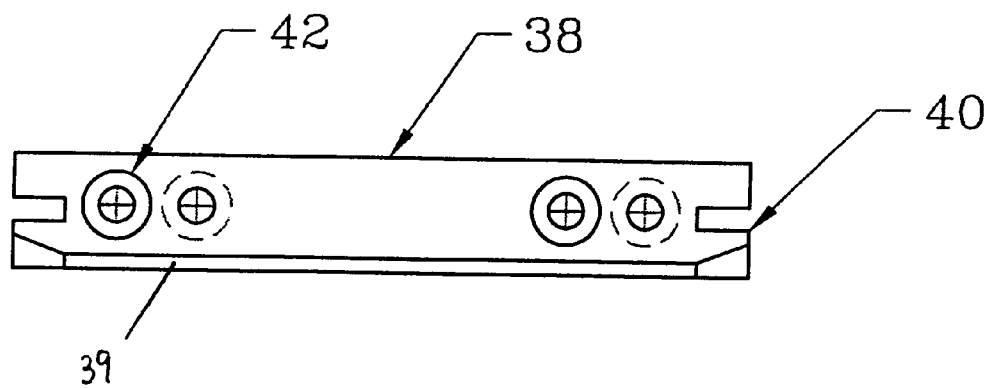
FIG. 2A is a plan view of an expander tail of the present invention.
Figure 2B:
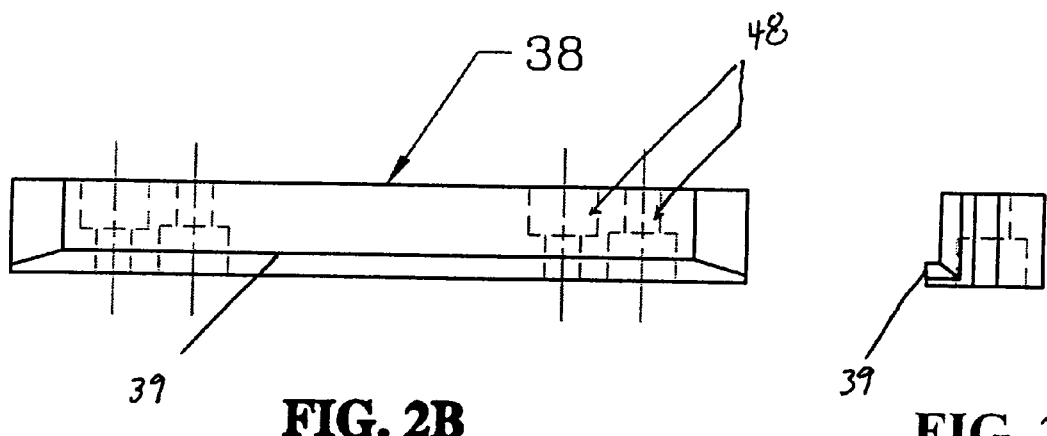
FIG. 2B is a side view of an expander rail of the present invention.
Figure 2C:
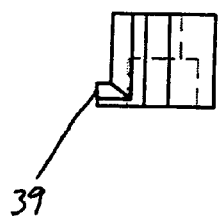
FIG. 2C is an end view of an expander rail of the present invention.
Figure 8:
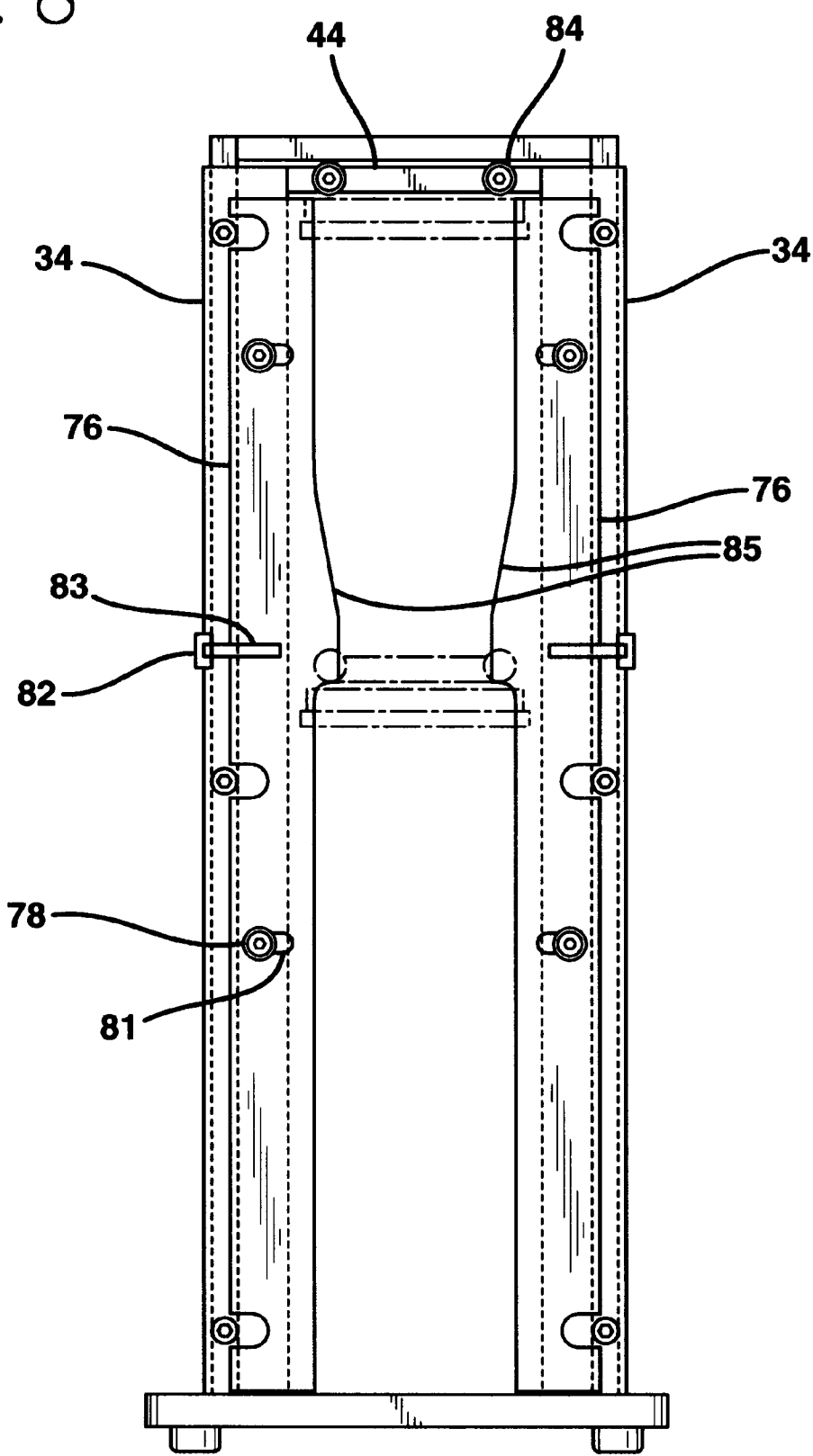
FIG. 8 is a front view of the unload limit gates of the present invention.

FIG. 8 is an elevation view of the expander housing looking into the open front area 26. A pair of unload limit gates 76 are mounted on shoulder screws 78 which attach to the two front angular end caps 34. A pair of gate support angles 80 (as shown in FIG. 2A), similar to end caps 34, are held in place by the same shoulder screws 78. The gates fit just loosely enough to freely move horizontally along the shoulder screws, limited in travel by the length of each gate slot 81. A compression spring 82 is located within a captive slot 83 in each gate and is held in place by spring well blocks attached to the edge of both walls 24. The springs load each gate inward. Two bearing rollers 84 are attached to the moving top plate 44 which, when in the up position, allows each gate to remain in the closed position (as in FIG. 8). When handle 46 is pushed down for stack compression, the travel of rollers 84 down along the inside edge of the gates contacts the angled surfaces 85 thereby forcing the gates out and open. When a plurality of plates is pushed into the expanded housing unit from the magazine loading nest, the unload limit gates create a backstop, beyond which the plates can not be moved. Once the expander unit is compressed and subsequently, the unload gates open, a stack of multiwell plates may be transferred freely between the expander housing 22 and the loading nest 12.

Once the handle 46 is pulled to the maximum height, the handle can be held in position by a locking device 56 located on the top of the housing 22 and its mating piece 54 located on the top plate 44, for example a ball knob/slide lock 56 as shown in FIGS. 3 and 4.

The magazine nest 16 is located behind the expander unit 14 and comprises a portion of the base 18 from which a pair of alignment pins 60 are attached. A multiwell plate magazine from an automated analysis instrument can be aligned properly by means of the mating of holes on the magazine base and the pins 60. The magazine is aligned such that the loading shelves of the magazine are in planar orientation with the rails of the extended expander unit.

Figure 5:
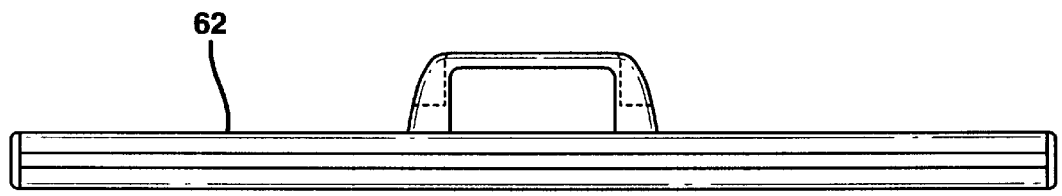
FIG. 5 is a side view of a stack loader intended for use with the present invention.

A manual stack loader 62, which is essentially a handled stick as shown in FIG. 5, may be used to transfer the plates from the extended expander unit to the magazine. The stack loader is held in vertical position and against the plates. Once the extender unit is fully extended and a magazine is aligned to receive the plates, an operator pushes the plates into the magazine all at once with the loader 62.

Figure 6:
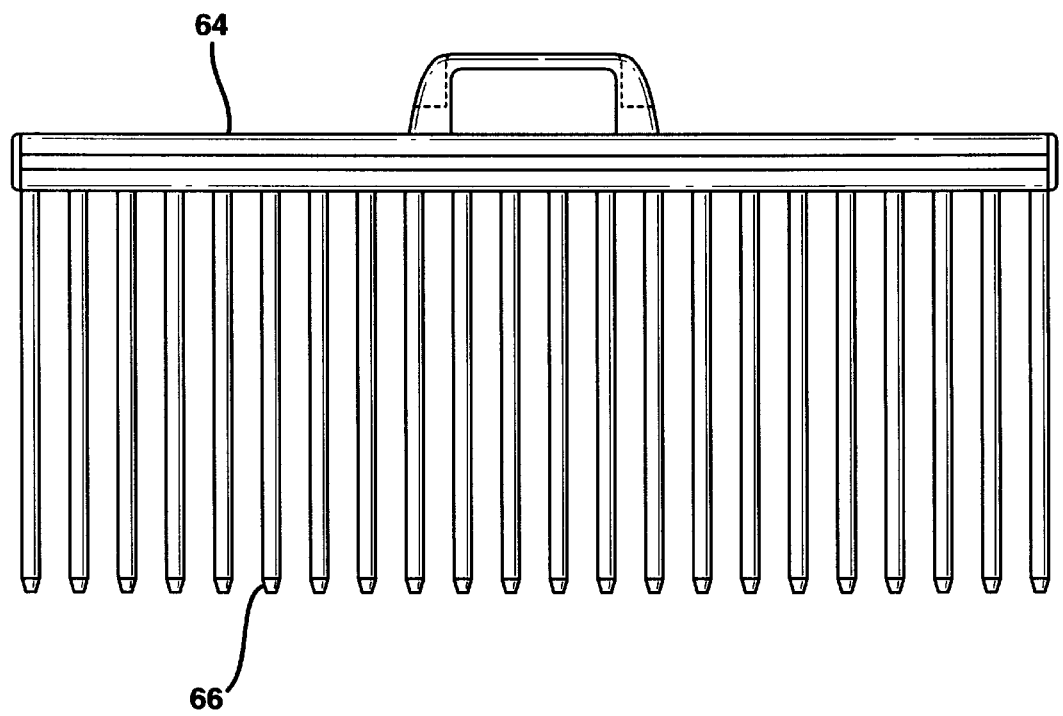
FIG. 6 is a side view of a magazine unloader intended for use with the present invention.

In order to unload a fully loaded magazine back into the expander unit 14, a manual stack unloader 64, as shown in FIG. 6 may be employed. The stack unloader 64 is a multi-toothed comblike structure, each tooth 66 sized to fit into the slots in a magazine, behind the plates. The plates are transferred from the magazine by sliding the unloader horizontally toward the expander unit 14. Once situated in the extended expander unit, the handle 46 is unlocked and depressed. The plates contact one another reforming a stack, and can thereafter be removed by hand from the depressed expander unit.

Although the invention has been described in detail for the purpose of illustration, it is understood that such detail is solely for that purpose and variations can be made therein by those skilled in the art without departing from the spirit and scope of the invention which is defined by the following claims.

What is claimed:

1. A device for separating plates from a stack of multiwell plates for input into a magazine loader or stacking multiwell plates taken from a magazine loader comprising;

a housing having at least two opposing side supports defining an open front and back, that accepts a stack of multiwell plates;

a plurality of expander rails located along the interior of said side supports and defining slots capable of fitting between individual plates of said stack multiwell plates; and a plurality of pins slidably connecting said expander rails, whereby when a topmost expander rail is pulled upward, subsequent expander rails separate a distance commensurate with the length of said pins;

a device for separating plates from a stack of multiwell plates for input into a magazine loader further comprising a pair of load limit gates attached to opposing ends of said housing and extending into said open back such that said gates are capable of opening to allow passage of said multiwell plates therethrough.

2. The device of claim 1 further comprising a stack loader whereby said stack loader is capable of locating said stack within said housing, and forcing an expanded stack out of said housing through said open back.

3. The device of claim 1 wherein a maximum distance between said expander rails is substantially equal to a distance between individual slots in said magazine loader.

4. A method of loading a plurality of stacked multiwell plates to a magazine loader having a plurality of slots for receiving multiwell plates, comprising the steps of:

a) providing a device for separating plates from a stack of multiwell plates for input into a magazine loader or stacking multiwell plates taken from a magazine loader comprising: a housing having at least two opposing side supports defining an open front and back, that accepts a stack of multiwell plates; a plurality of expander rails located along the interior of said side supports and defining slots capable of fitting between individual plates of said stack of multiwell plates; and, a plurality of pins slidably connecting said expander rails, whereby when a topmost expander rail is pulled upward, subsequent expander rails separate a distance commensurate with the length of said pins;

b) placing a stack of multiwell plates having steps between successive plates, into said housing such that said expander rails fit between said steps;

c) expanding the distance between said rails such that the distance between said rails is approximately equal to the distance between said slots in said magazine; and, d) transferring said multiwell plates to said slots of said magazine.

5. A method for unloading and stacking a plurality of multiwell plates from a loaded magazine loader having a plurality of slots for receiving multiwell plates, comprising the steps of:

a) providing a device for separating plates from a stack of multiwell plates for input into a magazine loader or stacking multiwell plates taken from a magazine loader comprising: a housing having at least two opposing side supports defining an open front and back, that accepts a stack of multiwell plates; a plurality of expander rails located alone the interior of said side supports and defining slots capable of fitting between individual plates of said stack of multiwell plates; and, a plurality of pins slidably connecting said expander rails, whereby when a topmost expander rail is pulled upward, subsequent expander rails separate a distance commensurate with the length of said pins;

b) transferring said plates from said loaded magazine to said housing such that said plates rest on individual expander rails;

c) decreasing the distance between said rails such that said multiwell plates contact each other and form a stack; and, d) removing said stack from said device.

6. A device for separating plates from a stack of multiwell plates for input into a magazine loader or stacking multiwell plates taken from a magazine loader comprising:

a housing having at least two opposing side supports defining an open front and back, that accepts a stack of multiwell plates;

a plurality of expander rails located along the interior of said side supports and defining slots capable of fitting between individual plates of said stack of multiwell plates; and a plurality of pins slidably connecting said expander rails, whereby when a topmost expander rail is pulled upward, subsequent expander rails separate a distance commensurate with the length of said pins.

7. A device for separating plates from a stack of multiwell plates for input into a magazine loader or stacking multiwell plates taken from a magazine loader comprising;
- a housing having at least two opposing side supports defining an open front and back, that accepts a stack of multiwell plates;
- a plurality of expander rails located along the interior of said side supports and defining slots capable of fitting between individual plates of said stack multiwell plates; and
- a plurality of pins slidably connecting said expander rails, whereby when a topmost expander rail is pulled upward, subsequent expander rails separate a distance commensurate with the length of said pins; and
- a device for separating plates from a stack of multiwell plates for input into a magazine loader further comprising a pair of unload limit gates attached to opposing ends of said housing and extending into said open front such that said gates are capable of opening to allow passage of said multiwell plates therethrough.

* * * * *